(12) United States Patent
Takayama

(10) Patent No.: US 8,253,783 B2
(45) Date of Patent: Aug. 28, 2012

(54) ELECTRONIC ENDOSCOPE SIGNAL-PROCESSING DEVICE AND ELECTRONIC ENDOSCOPE SYSTEM

(75) Inventor: Shinichi Takayama, Tokyo (JP)

(73) Assignee: Hoya Corporation, Tokyo (JP)

( * ) Notice: Subject to any disclaimer, the term of this patent is extended or adjusted under 35 U.S.C. 154(b) by 483 days.

(21) Appl. No.: 12/497,871

(22) Filed: Jul. 6, 2009

(65) Prior Publication Data
US 2010/0007724 A1   Jan. 14, 2010

(30) Foreign Application Priority Data

Jul. 8, 2008   (JP) ................................. 2008-177943
Oct. 24, 2008   (JP) ................................. 2008-274566

(51) Int. Cl.
*A62B 1/04*   (2006.01)
(52) U.S. Cl. ...................... 348/65; 382/167; 348/222.1
(58) Field of Classification Search ............. 348/43–65, 348/222.1, 675; 353/84; 349/33; 382/167
See application file for complete search history.

(56) References Cited

U.S. PATENT DOCUMENTS

| | | | | |
|---|---|---|---|---|
| 5,081,524 A | * | 1/1992 | Tsuruoka et al. | ............. 348/675 |
| 7,454,056 B2 | * | 11/2008 | Hayaishi | ..................... 382/167 |
| 2002/0145661 A1 | | 10/2002 | Takahashi et al. | |
| 2006/0211915 A1 | | 9/2006 | Takeuchi et al. | |
| 2007/0153542 A1 | | 7/2007 | Gono et al. | |
| 2007/0177029 A1 | * | 8/2007 | Wada et al. | ................. 348/222.1 |
| 2007/0216876 A1 | * | 9/2007 | Narikawa | ......................... 353/84 |
| 2009/0027577 A1 | * | 1/2009 | Nose | ................................ 349/33 |
| 2009/0109284 A1 | | 4/2009 | Takayama | |

FOREIGN PATENT DOCUMENTS

| | | |
|---|---|---|
| JP | 2006-61620 | 3/2006 |
| JP | 2006-239206 | 9/2006 |

OTHER PUBLICATIONS

English language Abstract of JP 2006-61620, Mar. 9, 2006.
English language Abstract of JP 2006-239206, Sep. 14, 2006.

* cited by examiner

*Primary Examiner* — Sath V Perungavoor
*Assistant Examiner* — Nathnael Aynalem
(74) *Attorney, Agent, or Firm* — Greenblum & Bernstein, P.L.C.

(57) ABSTRACT

An electronic endoscope signal-processing device is provided that includes a gradation compensation processor. The gradation compensation processor compensates for R, G, and B gradations by controlling R, G, and B tone curves defining relationship between input values and output values of each of the R, G, and B signals. The R tone curve is shaped so as to squash the output values of the R Signal when the R signal input values are in a relatively low range and to expand the output values when the input values are in a relatively high range.

4 Claims, 11 Drawing Sheets

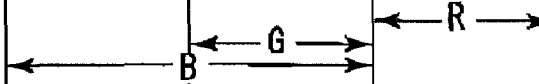

BEFORE PROCESSING

AFTER PROCESSING

AFTER PROCESSING

FIG. 8A

BEFORE PROCESSING

| ESOPHAGUS | LOW | MIDDLE | HIGH |
|---|---|---|---|
| NORMAL MUCOUS MEMBRANE | | ←G→ ←B→ | ←—R—→ |
| FADE AWAY IMAGE | | ←——B——→ | ←——G——→ ←—R—→ |

FIG. 8B

AFTER PROCESSING

| ESOPHAGUS | LOW | MIDDLE | HIGH |
|---|---|---|---|
| NORMAL MUCOUS MEMBRANE | ←----R----→ | ←G→ ←B→ | ◯ — A9 |
| FADE AWAY IMAGE | ←----R----→ | ←—B—→ ←—G—→ | ⬭ — A10 |

ELECTRONIC ENDOSCOPE SIGNAL-PROCESSING DEVICE AND ELECTRONIC ENDOSCOPE SYSTEM

BACKGROUND OF THE INVENTION

1. Field of the Invention

The present invention relates to signal-processing for an electronic endoscope system.

2. Description of the Related Art

There is known an electronic endoscope system that uses narrow band illumination to obtain a spectral image of a particular band for enhancing features such as blood vessels, lesioned areas, and the like, as disclosed in Japanese Unexamined Patent Publication No. 2006-061620. However, the system requires a specialized light source. Thus, this prior art structure raises the cost of the system and is at a disadvantage in carrying out the simultaneous observation of a normal endoscopic image taken with white light. On the other hand, in Japanese Unexamined Patent Publication No. 2006-239206, a spectral image is emulated from white light by applying a matrix corresponding to the above-mentioned narrow band, to a color transformation matrix which is normally used in image processing.

SUMMARY OF THE INVENTION

However, the image processing disclosed in Japanese Unexamined Patent Publication No. 2006-239206 is complicated, and moreover, it is difficult to emulate a desired spectral image with a linear transformation unless you use a stepwise linear curve. Therefore, features of a target for observation, such as a lesion, may not be sufficiently enhanced. For example, in endoscopy, the lesion may be identifiable by a pattern of distributed blood vessels. However, the image processing in Japanese Unexamined Patent Publication No. 2006-239206 cannot effectively distinguish the blood vessels from the surrounding tissue, thus requiring comparison with a normal spectrum image for an appropriate diagnosis.

Therefore, an object of the present invention is to sufficiently enhance images of a blood vessel or lesion using white light illumination in an electronic endoscope system.

According to the present invention, an electronic endoscope signal-processing device is provided that includes a gradation compensation processor.

The gradation compensation processor compensates for R, G, and B gradations by controlling R, G, and B tone curves defining a relationship between input values and output values of each of the R, G, and B signals. The R tone curve is shaped so as to squash the output values of the R signal when the input values of the R signal are in a relatively low range, and to expand the output values when the input values are in a relatively high range.

BRIEF DESCRIPTION OF THE DRAWINGS

The objects and advantages of the present invention will be better understood from the following description, with reference to the accompanying drawings in which:

FIGS. 6A-6C illustrate image-enhancing processes for stomachs;

FIGS. 8A-8B illustrate image-enhancing processes for esophagi;

DESCRIPTION OF THE PREFERRED EMBODIMENTS

Figure 1:
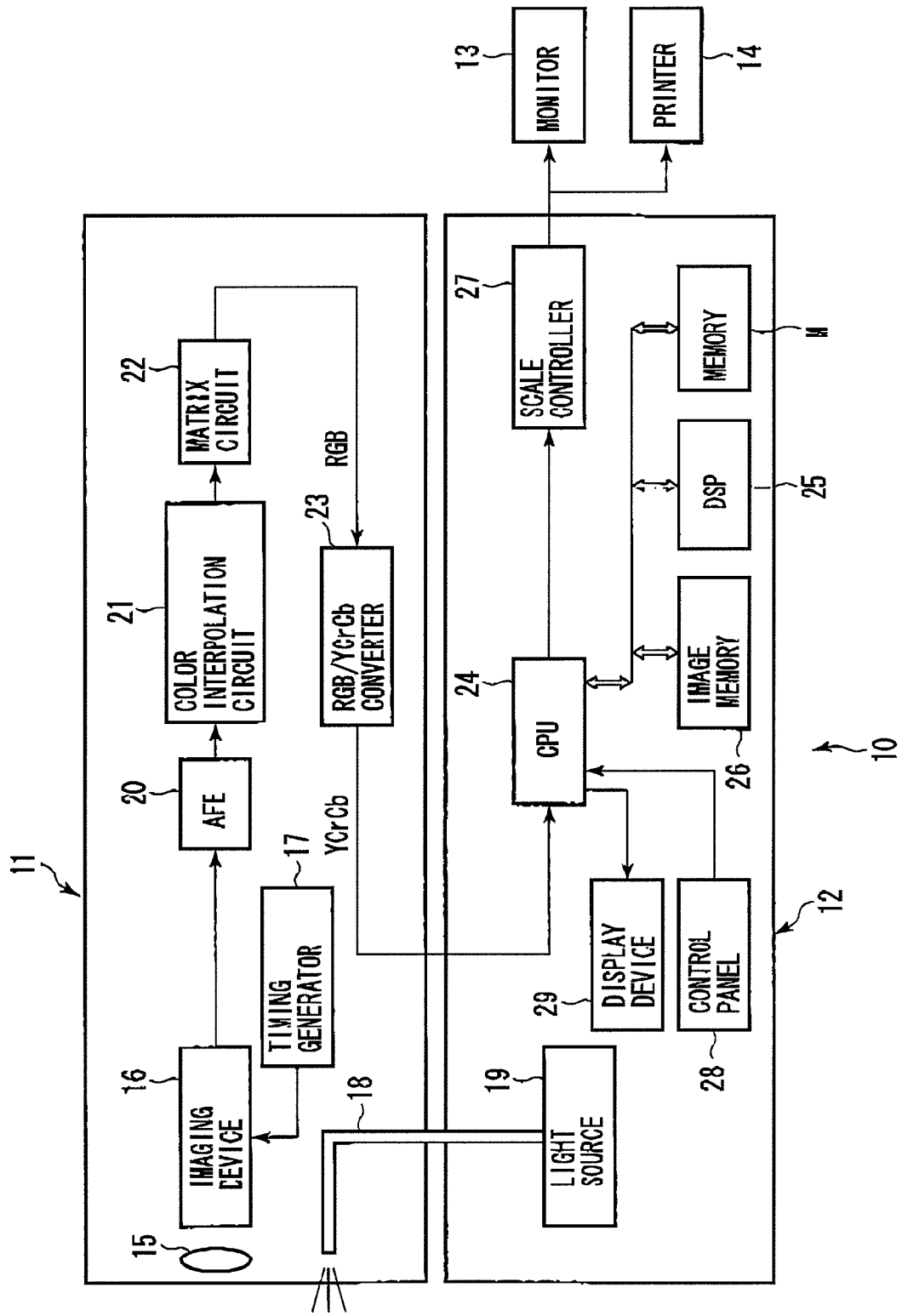
FIG. 1 is a block diagram schematically illustrating the general structure of an electronic endoscope system of an embodiment.

The present invention is described below with reference to the embodiments shown in the drawings.

FIG. 1 is a block diagram which schematically illustrates the general structure of an electronic endoscope system of an embodiment to which the present invention is applied.

As is well know in the art, the electronic endoscope system 10 generally includes a scope portion 11 having a flexible tube for insertion into a body, a processing unit 12 to which the scope portion 11 is detachably attached and that receives image signals from the scope portion 11 so as to carry out image processing, and output device(s) such as a monitor 13 to display the images from the processing unit 12 and/or a printer 14 to record the images.

A photographic lens 15 and an imaging device 16 are provided at the distal end of the flexible tube of the scope portion 11. A timing generator 17, which may be provided inside the scope portion 11, drives the imaging device 16. The imaging device 16 captures images inside the body with white light, which may be supplied from a light source 19 provided inside the processing unit 12 through a light guide fiber 18.

The analog image signals of the RGB complementary colors obtained by the imaging device 16 are converted into digital image signals at an analog front end circuit 20 and then converted into RGB signals through a color-interpolation circuit 21 and a matrix circuit 22. The RGB signals are then converted into YCrCb signals at an RGB/YCrCb converter 23 and fed to the processing unit 12.

The YCrCb signals, which are input to the processing unit 12 are then, for example, fed to a DSP 25 via a CPU 24. The YCrCb signals are subjected to image processing, such as contour compensation and the like, at the DSP 25 and converted into the RGB signals. The RGB signals are then temporally stored in a (volatile) image memory 26. Then, the RGB signals are subjected to predetermined gradation compensation processes at the DSP 25 with respect to data stored in (non-volatile) memory M under instructions from the CPU 24, and in turn are fed to a scale controller 27. The RGB signals, which have been compensated for gradation, are then fed to a scale controller 27, and are subsequently subjected to size compensation that is carried out on the basis of the image size, and then output to the monitor 13 or the printer 14.

A control panel 28 and a display device 29, such as an LCD monitor, are also connected to the CPU 24, such that a GUI with keys on the control panel 28 and display device 29 may be provided. In other words, the user may select a mode or set a variety of items by operating the control panel 28 while looking at the display device 29.

Figure 2:
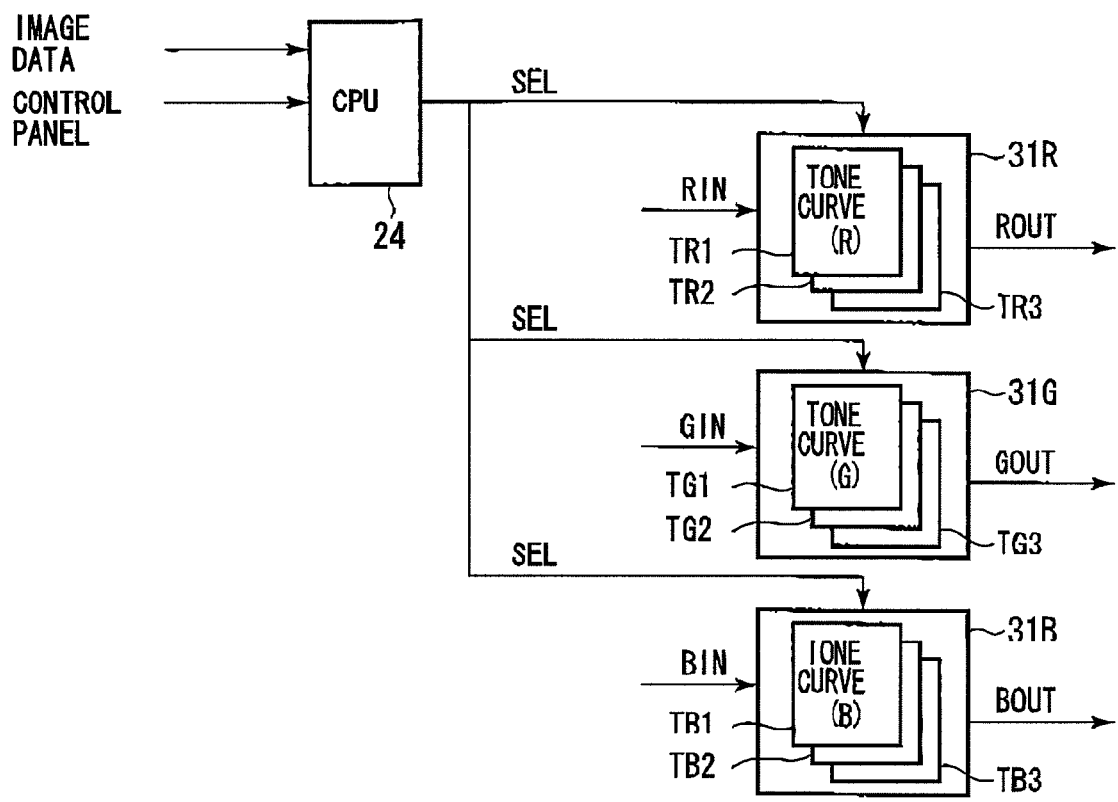
FIG. 2 is a block diagram that schematically illustrate the concept of the gradation compensation processes.
Figure 3:
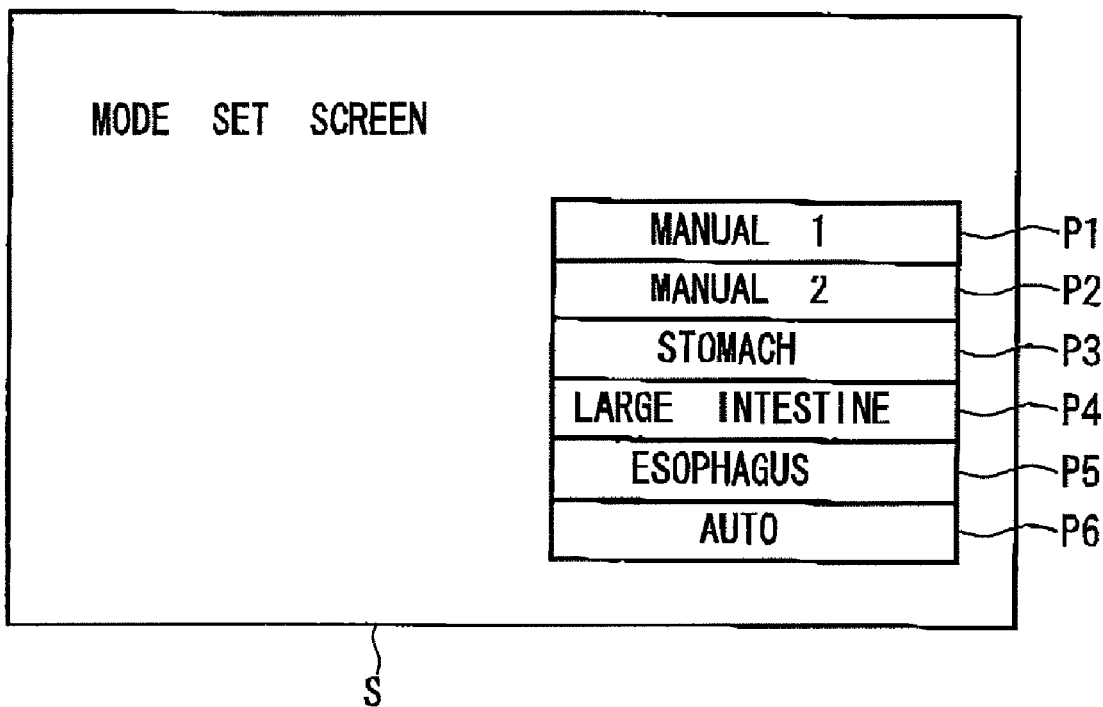
FIG. 3 is an example of an operational menu to select one of the gradation compensation processes or mode.

With reference to FIGS. 2 and 3, the gradation compensation processes of the present embodiment are next explained.

FIG. 2 is a block diagram that schematically illustrates the concept of the gradation compensation processes. FIG. 3 gives an example of an operational menu, i.e., a screen for selecting one of the gradation compensation processes, displayed on the display device 29.

For each of R-signal RIN, G-signal GIN, and B-signal BIN, a corresponding gradation compensation process is separately executed. Namely, an R-gradation compensation 31R is executed for the R-signal RIN, a G-gradation compensation 31G for the G-signal GIN, and a B-gradation compensation 31B for the B-signal BIN. Each of the R-gradation compensation, G-gradation compensation, and B-gradation compensation includes a plurality of gradation compensation pattern which are stored in the memory M as tone curves.

FIG. 2 schematically illustrates an example situation in which the R-gradation compensation includes tone curves TR1-TR3, the G-gradation compensation includes tone curves TG1-TG3, and the B-gradation compensation includes tone curves TB1-TB3. In FIG. 2, combinations of the RGB tone curves (TR1, TG1, TB1), (TR2, TG2, TB2), and (TR3, TG3, TB3) are bound together as one set, and thereby, one set of RGB tone curve combinations is selected according to a selection signal SEL. In the present embodiment, six set of the RGB tone curve combinations or more are prepared for six observation modes, which will be discussed later. However, each of the tone curves may be stored in the memory M as equations specified by compensation parameters, and a lookup table may also be used.

The gradation compensation processes according to the selected combination of the RGB tone curves are carried out for each of the R-signal RIN, C-signal GIN, and B-signal BIN, and in turn, compensated KGB signals are output to the scale controller 27 (see FIG. 1), as R-signal ROUT, G-signal GOUT, and B-signal BOUT, respectively. Note that in the present embodiment, the gradation compensation is carried out on each of the R, G, and B signals to enhance pit patterns of the stomach, blood vessels in the large intestine, and the like, according to the organ under observation.

Tone curves are selected by means of an observation mode in the operational menu displayed on the display device 29. As shown in FIG. 3, boxes P1-P6, which correspond to a plurality of observation modes (e.g., six modes) are indicated on the screen S of the display device 29. One of the boxes P1-P6, which corresponds to a desired observation mode, can be selected by the user's key operation on the control panel 28 (see FIG. 1). In the present embodiment, examples of the observation modes include two manual modes (P1 and P2), and modes specific to particular organs, such as a stomach mode (P3), a large intestine mode (P4), and an esophagus mode (P5), and an automatic mode (P6) which automatically identifies an observation target and carries out gradation compensation adapted to the identified target.

The manual modes (P1 and P2) are the modes in which the user manually compensates for the respective R, G, and B gradation, and are available for storing the corresponding compensation parameters in memory, such that the RGB gradation compensation processes can later reference the compensation parameters adjusted by the user. The stomach mode (P3), the large intestine mode (P4), and the esophagus mode (P5) are the RGB compensation modes which apply the compensation parameters which were adjusted for the stomach, the large intestine, and the esophagus, and stored in the memory M, before the device is shipped. Furthermore, the automatic mode (P6) applies a certain image processing, a pattern-matching process, and the like, to images being captured by the imaging device 16, to automatically identify a type of target, and applies the RGB compensation processes with the compensation parameters (previously stored in the memory M) adjusted to the specified target or organ. Another example target organ besides the stomach, the large intestine, and the esophagus, could be the lungs.

The CPU 24 selects an observation mode in accordance with a signal from the control panel 28 and outputs the selection signal SEL, corresponding to the selected observation mode, to the DSP 25. The DSP 25 retrieves the compensation parameters corresponding to the selection signal SEL from the memory M to carry out the RGB gradation compensation. Incidentally, when the automatic mode (P6) is selected, the CPU 24 carries out a feature extraction to an image data stored in the image memory 26 to identify the subject under observation according to its pattern, and outputs the selection signal SEL corresponding to the specified target or organ. For example, the identification of the target, as in the case of the stomach, may be carried out by detecting patterns inside the mouth or of patterns of Barrett's. And in case of the large intestine, it may be detected by extracting patterns of haustra. Namely, the identification is accomplished by detecting a distinctive pattern in each organ.

On the other hand, when an observation mode without any RGB gradation compensation is selected by operation of a key on the operational panel 29, such as by pressing a certain key button, the R, G, and B signals are fed to the scale controller 27 without being subjected to any RGB gradation compensation processes at the DSP 25.

Figure 4:
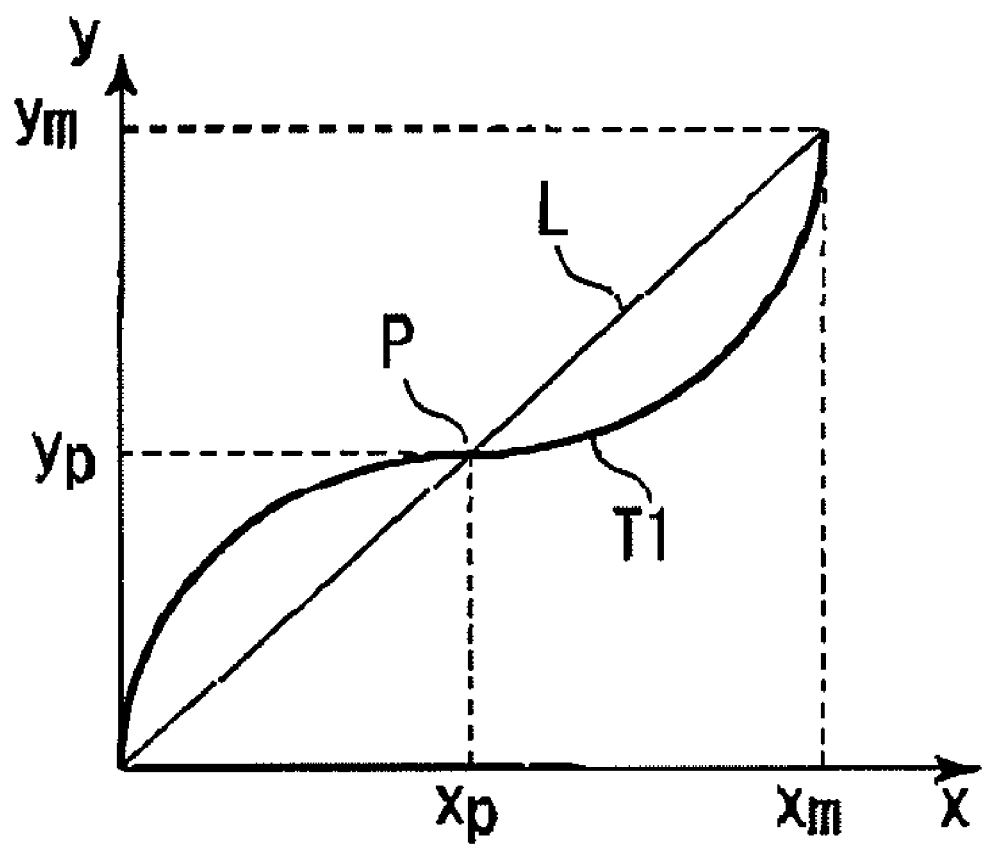
FIG. 4 gives an example of such tone curve.
Figure 5:
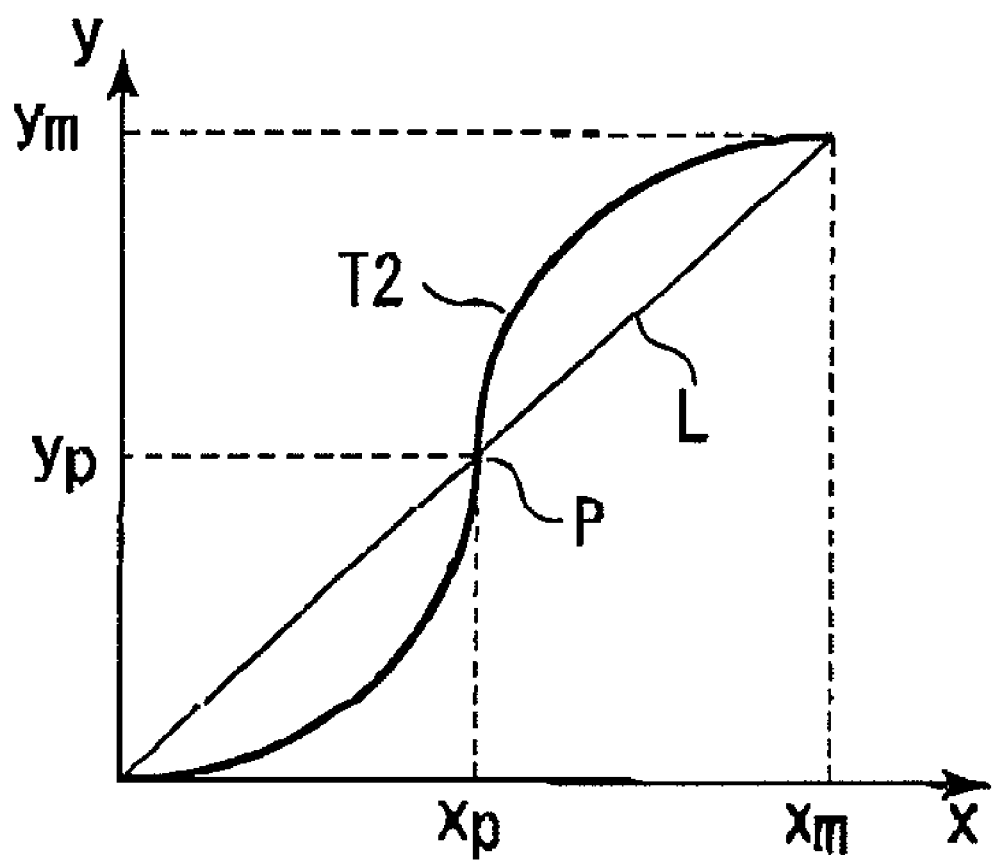
FIG. 5 gives another example of such a tone curve.

Referring to FIGS. 4 and 5, the principle of the RGB gradation compensation processes of the present embodiment will be explained.

Distribution of luminance in an image captured by the electronic endoscope may generally be similar to the normal distribution. However, distribution of histograms for each R, G, and B color component depends on features of the observing portion, such as structural patterns, vessel patterns, and their size. In the present embodiment, the R, G, and B tone curves are controlled so as to compensate for the R, G, and B gradation, and thus, so as to transform the histograms of the R, G, and B color components such that they enhance the peculiar features (e.g., the structural patterns and blood vessel patterns of the subject under observation), in order to facilitate observation.

In general, when dispersion of the histogram for a certain color component is small, the pixel values of the color component concentrate about the mean value, and the image of the color has high contrast. Therefore, when a transformation to reduce the dispersion of the histogram is carried out on a certain color component, the patterns mainly composed of this color component will be visually enhanced. On the other hand, when dispersion of the histogram for a certain color component is large, the image has low contrast. Therefore, when a transformation to increase the dispersion of the histogram is carried out on a certain color component, the patterns mainly composed of this color component will be blurred, and in turn patterns composed of the other colors will be relatively enhanced.

In the present embodiment, the dispersion of the histogram of each of the R, G, and B color components is altered and the distribution is shifted by controlling the tone curve for each of the R, G, and B color components FIG. 4 and FIG. 5 illustrate two types of exemplary patterns of the tone curve that may be contemplated to be applicable to the present embodiment. In the present embodiment, these two types of tone curves for each of the R, G, and B color components are suitably modified and combined with each other, so as to suitably compensate for the RGB gradations.

In FIG. 4 and FIG. 5, line L is straight line represented by y=x and corresponds to the case when no gradation compensation is carried out. A point P, which is represented by coordinates x=xp and y=yp, is an intersection of tone curves T1 and T2 with the line L. Furthermore, x=xm represents the maximum value (e.g., 255) of the input pixel values and y=ym represents the maximum value (e.g., 255) of the output pixel values.

As is apparent from FIG. 4 and FIG. 5, the output pixel values are concentrated in an area where the slope of the tangent or the derivative of the tone curve is greater than 1, and are spread in an area where the slope of the tangent or the derivative is less than 1. As denoting the tone curve T1 of FIG. 4 as $y=f1(x)$, the function $f1(x)$ is a continuous function that satisfies $x<f1(x)$ in $0<x<xp$ and $x>f1(x)$ in $xp<x<xm$. Namely, the slope of the function $f1(x)$ at $x=xp$ is less than 1, i.e., the derivative $f1'(xp)<1$, and therefore, the output pixel values about the intersection P are dense (i.e., concentrated). Furthermore, the derivative $f1'(x)$ of the tone curve T1 is greater than 1 ($f1'(x)>1$), around $x=0$ and $x=xm$, and thus the output pixel values around the minimum pixel value and the maximum pixel value are transparent (spread).

On the other hand, when denoting the tone curve T2 of FIG. 5 as $y=f2(x)$, the function $f2(x)$ is a continuous function that satisfies $x>f2(x)$ in $0<x<xp$ and $x<f2(x)$ in $xp<x<xm$. Namely, the slope of the function $f2(x)$ at $x=xp$ is greater than 1, i.e., the derivative $f2'(xp)>1$, and therefore, the output pixel values about the intersection P are transparent (i.e., spread). Furthermore, as for the tone curve T2, the derivative $f2'(x)$ is less than 1 ($f2'(x)<1$), around $x=0$ and $x=xm$, and thus the output pixel values around the minimum pixel value and the maximum pixel value are dense (concentrated).

Next, with reference to FIGS. 6-8, principles of the image-enhancing processes (color transformation processes) used to enhance lesioned areas in the stomach, the large intestine, and the esophagus will be explained. Note that FIGS. 6-8 are figures intended to illustrate the image-enhancing processes for stomachs, large intestines, and esophagi, respectively.

In general, as for images captured inside a body, regardless of the location, the rate of the R-color component in the luminance signal is high compared to those of the G and B-color components. Therefore, in the image-enhancing process of the present embodiment, the control of the R-color component substantially corresponds to a luminance contrast control, and the control of the G and B-color components substantially correspond to a hue contrast control.

FIG. 6A schematically illustrates the distribution of the R, G, and B pixel values for an image normally obtained when capturing an image inside a stomach (a normal mucous membrane image) and for an image substantially including ductal structure which is peculiar to lesioned areas inside the stomach (a ductal structure image). Namely, it shows areas where the distribution of each histogram of the R, G, and B pixel values for the normal mucous membrane image and the ductal structure image concentrates before the image-enhancing processes of the present embodiment is carried out.

As for the R-color pixel values, the pixel values substantially concentrate in a high range in both of the normal mucous membrane image and the ductal structure image. On the other hand, as for the G-color pixel values, the values substantially concentrate in a middle range of the normal mucous membrane image, and substantially concentrate in the middle range and to the high range of ductal structure image. Furthermore, as for the B-color pixel values, the values substantially concentrate in a low range and the middle range of the normal mucous membrane image, and substantially concentrate in the middle range and the high range of the ductal structure image.

FIG. 6B schematically indicates how R, G, and B pixel values of the normal mucous membrane image and the ductal structure image, in FIG. 6A, are changed by the image processing for the R component in the stomach mode of the present embodiment. In the image processing for the R component, the R component pixel values in the middle range and the high range are transformed to pixel values in the low range and the middle range (where the distribution is narrowed). As for the normal mucous membrane image of the stomach, the most part of pixel values in the high range are of the R-component, therefore, with the above image processing, pixels having the pixel value within the high range almost fade-away and the image gets dark (an area A1). On the other hand, as for the ductal structure image of the stomach, there also exist many pixels of the G-color component and the B-color component with a pixel value within the high range, therefore, the image is kept relatively bright even though the pixel values of the R-component within the high range have almost faded away (an area A2).

Consequently, by applying the above-mentioned image processing to an endoscopic image captured inside a stomach, such that transforming the pixel values of the R-component within the middle range and the high range to the low range and the middle range (narrowing the distribution), the luminance contrast is enhanced between areas including the ductal structure and the remaining areas including the normal mucous membrane. Therefore, the image areas, which substantially include the ductal structure, are brightly enhanced compared with the surrounding areas.

FIG. 6C schematically indicates how R, G, and B pixel values of the normal mucous membrane image and the ductal structure image, in FIG. 6A, are changed by the image processing for the G and B component in the stomach mode of the present embodiment. In the present embodiment, the pixel values of the G and B components in the middle range are transformed to pixel values in the low range and the high range (with separated distribution). For example, the pixel values are transformed to either of the low range or the high range with a predetermined value in the middle range being set as a boundary.

In the middle range of the normal mucous membrane image, pixel values of the B and G color components are distributed mainly over the relatively low area of the middle range. On the other hand, in the middle range of the ductal structure image, pixel values of the B and G color components are distributed mainly over the relatively high area of the middle range. Therefore, by appropriately setting the above-mentioned predetermined value, the G and B components of the normal mucous membrane image in the middle range are transformed to pixel values in the low range, and the G and B components of the ductal structure image in the middle range are transformed to pixel values in the high range. Namely, pixel values of the G and B components in the middle range of the endoscopic image captured inside the stomach are separated whereby the normal mucous membrane image is transformed substantially to the low range (an area A3) and the ductal structure image is transformed substantially to the high range (an area A4).

Thereby, as for image areas that substantially include the normal mucous membrane image, the G and B color components are substantially distributed in the low range, and as for image areas that substantially include the ductal structure image, the C and B color components are substantially distributed in the high range. Therefore, the C and B components of areas substantially including the ductal structure image of the endoscopic image captured inside the stomach, are enhanced and the hue contrast is emphasized.

Figure 7A:
FIGS. 7A-7C illustrate image-enhancing processes for large intestines.
Figure 7B:
Figure 7C:
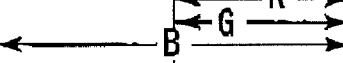

With reference to FIGS. 7A-7C, the image-enhancing process for the large intestine will be explained. FIG. 7A schematically illustrates the distribution of the R, G, and B pixel values for an image normally obtained when capturing an image inside the large intestine (a normal mucous membrane image) and for an image substantially including a pit pattern which is peculiar to lesioned areas inside the large intestine (a pit pattern image). Namely, it shows areas where the distribution of each histogram of the R, G, and B pixel values for the normal mucous membrane image and the pit pattern image concentrates before the image-enhancing processes of the present embodiment is carried out.

The pixel values of the R-color component of the normal mucous membrane image in the large intestine substantially concentrate in the middle range and the high range, and the R-color pixel values of the pit pattern image substantially concentrate in the high range. On the other hand, the G-color pixel values substantially concentrate in the middle range and the lower side of the high range of the normal mucous membrane image, and substantially concentrate in the high range of pit pattern image. Furthermore, as for the B-color pixel values, the values substantially concentrate in the middle range of the normal mucous membrane image, and substantially concentrate over the middle range and the high range of the pit pattern image.

FIG. 7B schematically indicates how R, G, and B pixel values of the normal mucous membrane image and the pit pattern image, in FIG. 7A, are changed by the image processing for the R component in the large intestine mode of the present embodiment. In the image processing for the R component, as similar to that of the stomach mode, the R component pixel values in the middle range and the high range are transformed to pixel values in the low range and the middle range (the distribution is narrowed). As for the normal mucous membrane image of the large intestine, although there also exist some pixels of the G-component having the pixel values in the high range, the majority of pixel values in the high range are of the R-component. Therefore, with the above image processing, pixels having a value within the high range almost fade-away and the image gets dark (an area A5). On the other hand, as for the pit pattern image of the large intestine, there also exist many pixels of the G-color component and the B-color component with the pixel value within the high range, therefore, the image is kept relatively bright even though the pixel values of the R-component within the high range have almost faded away (an area A6).

Consequently, by applying the above-mentioned image processing to an endoscopic image captured inside a large intestine, such that transforming the pixel values of the R-component within the middle range and the high range to the low range and the middle range (narrowing the distribution), the luminance contrast is enhanced between areas including the pit pattern and the remaining areas including the normal mucous membrane. Therefore, the image areas, which substantially include the pit pattern, are brightly enhanced compared with the surrounding areas.

FIG. 7C schematically indicates how R. G, and B pixel values of the normal mucous membrane image and the pit pattern image, in FIG. 7A, are changed by the image processing for the G and B component in the large intestine mode of the present embodiment. In the present embodiment, the pixel values of the G and B components in the middle range are transformed to pixel values in the low range and the high range (i.e., the distribution is separated). For example, the pixel values are transformed to either of the low range or the high range with a predetermined value in the middle range being set as a boundary.

In the middle range of the normal mucous membrane image, pixel values of the B component are distributed mainly over a relatively low area of the middle range. Furthermore, although pixel values or the G component are distributed over the middle range and the high range, the center of the distribution is in the low area of the middle range. On the other hand, although pixel values of the B component of the pit pattern image are distributed over the middle range and the high range, the main part of the distribution exists above the upper range of the middle range. Therefore, by appropriately setting the above-mentioned predetermined value, the G and B components of the normal mucous membrane image are transformed to pixel values in the low range, and the G and B components of the pit pattern imago are transformed to pixel values in the high range. Namely, pixel values of the G and B components in the middle range of the endoscopic image captured inside the large intestine are separated by the image processing of the present embodiment for the C and B components, such that the normal mucous membrane image being transformed substantially to the low range (area A7), and the pit pattern image being transformed substantially to the high range (area A8).

Thereby, as for image areas that substantially include the normal mucous membrane image, the G and B color components are substantially distributed in the low range, and as for image areas that substantially include the pit pattern image, the G and B color components are substantially distributed in the high range. Therefore, the G and B components of areas substantially including the pit pattern image of the endoscopic image captured inside the large intestine, are enhanced and the hue contrast is emphasized as is the case also, in the stomach mode.

With reference to FIGS. 8A and 8B, the image-enhancing process for the esophagus will be explained. FIG. 8A schematically illustrates the distribution of the R, G, and B pixel values for an image normally obtained when capturing an image inside an esophagus (a normal mucous membrane image) and for an image substantially including a color fade-away area which is peculiar to lesioned areas inside the esophagus (a fade-away image). Namely, it shows areas where the distribution of each histogram of the R, G, and B pixel values for the normal mucous membrane image and the fade-away image concentrates before the image-enhancing processes of the present embodiment is carried out.

The pixel values of the R-color component of the normal mucous membrane image in the esophagus substantially concentrate in the middle range and the high range, and the R-color pixel values of the fade-away image substantially concentrate in the high range. On the other hand, the G and B color pixel values substantially concentrate in the middle range of the normal mucous membrane image, and substantially concentrate over the middle range and the high range of fade-away image.

FIG. 8B schematically indicates how R, G, and B pixel values of the normal mucous membrane image and the fade-away image, in FIG. 8A, are changed by the image processing for the R component in the esophagus mode of the present embodiment. In the image processing for the R component, as similar to that of the stomach mode and the large intestine mode, the R component pixel values in the middle range and the high range are transformed to pixel values in the low range and the middle range (the distribution is narrowed). As for the normal mucous membrane image of the esophagus, the most of the pixel values in the high range are of the R-component, therefore, with the above image processing, pixels having the pixel value within the high range almost fade-away and the image gets dark (an area A9). On the other hand, as for the fade-away image of the esophagus, there also exist many pixels of the G-color component and the B-color component with the pixel value within the high range, therefore, the image is kept relatively bright even though the pixel values of the R-component within the high range have almost faded away (an area A10).

Consequently, by applying the above-mentioned image processing to an endoscopic image captured inside an esophagus, such that transforming the pixel values of the R-component within the middle range and the high range to the low range and the middle range (i.e., narrowing the distribution) the luminance contrast is enhanced between areas including the fade-away image and the remaining areas including the normal mucous membrane. Therefore, the image areas, which substantially include the fade-away image, are brightly enhanced compared with the areas surrounding. Incidentally, in the esophagus mode, the pixel value transformations for the G and B components are not carried out.

Figure 9:
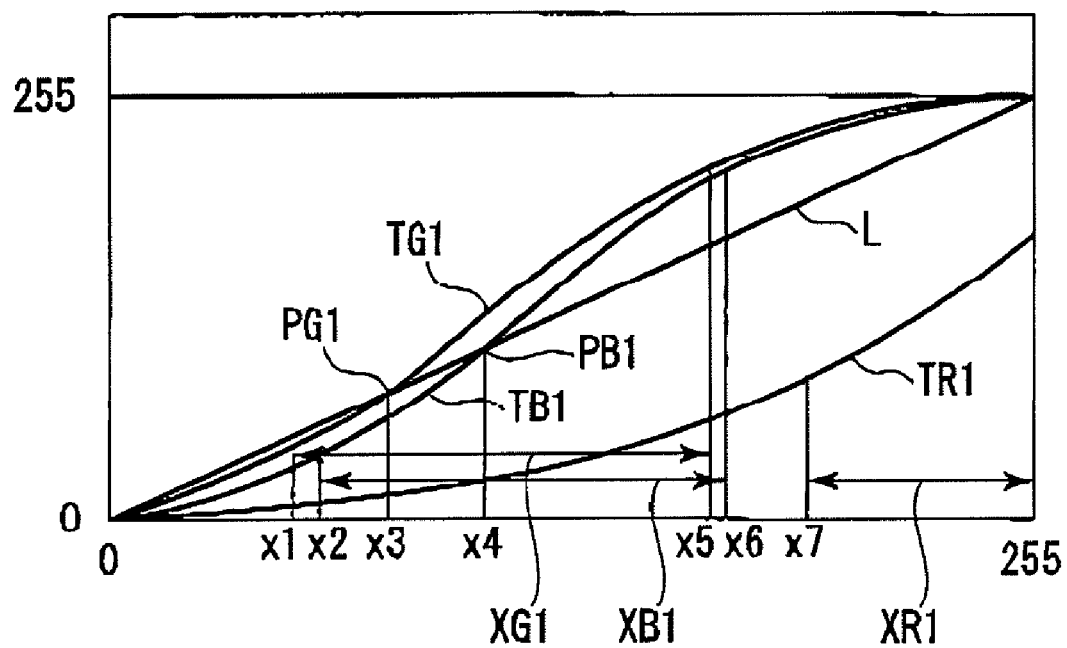
FIG. 9 gives examples of tone curves adjusted for digestive organs, including stomachs.
Figure 10:
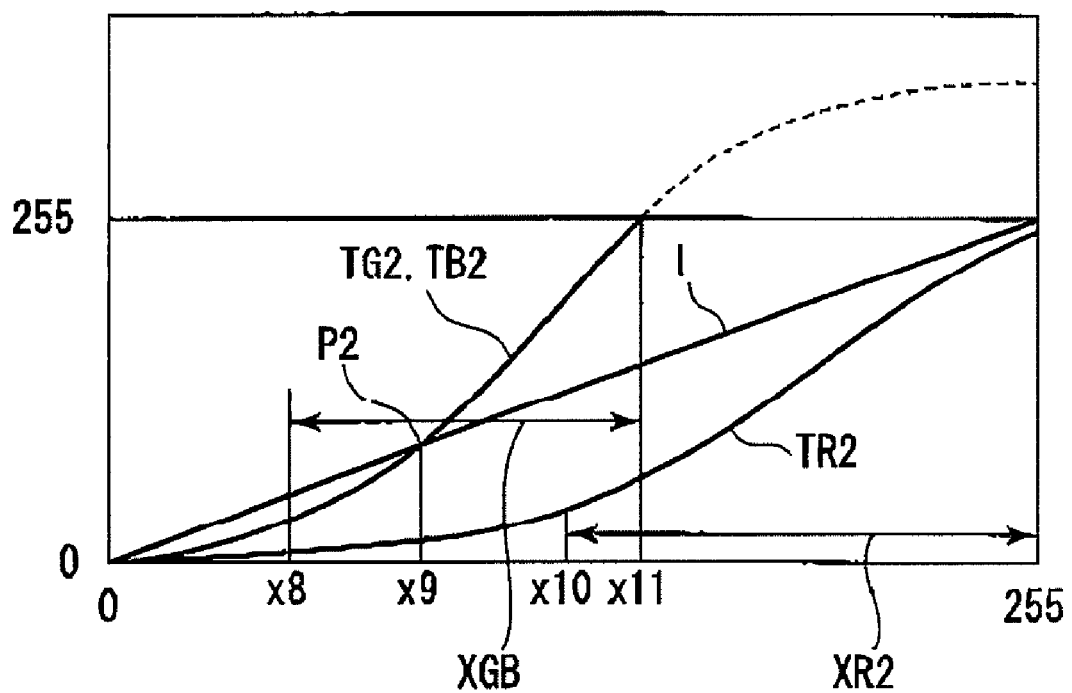
FIG. 10 gives examples of tone curves adjusted for large intestines.

Next, with reference to FIGS. 9-11, examples of the tone curves used in the image-enhancing processes in each of the above-mentioned modes will be explained. FIG. 9 gives an example of tone curves adjusted to digestive organs, including the stomach; FIG. 10 is for large intestines, and FIG. 11, for esophagi. In any of FIGS. 9-11, the abscissa represents the input pixel value x and the ordinate represents the output pixel value y, as is the case with FIG. 4 and FIG. 5 as well. Furthermore, the straight line L represents y=x, and the minimum value and the maximum value of both input and output pixel values are 0 and 255 (otherwise referred to as Xm), respectively.

Figure 11:
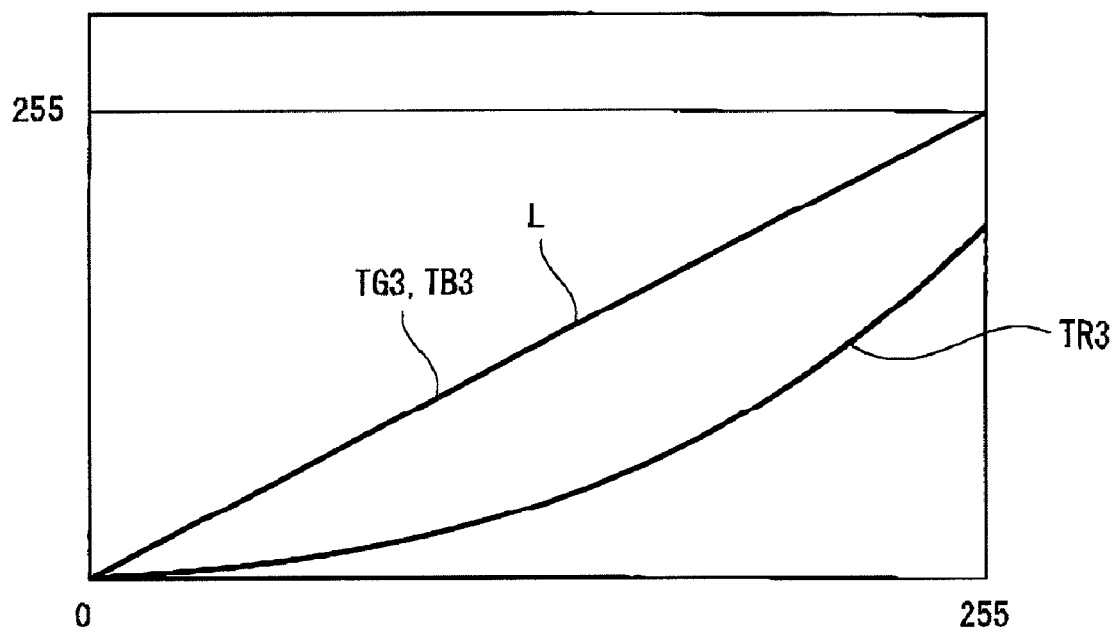
FIG. 11 gives examples of tone curves adjusted for esophagi.

Each of the R, G, and B tone curves in FIGS. 9 and 10 and the R tone curve in FIG. 11 may be represented by the function $f(x)=(A1-A2)/(1+\exp[(x-xd)/\alpha])+A2$, where A1, A2, and xd are parameters for adjusting the form of the curves. As for the R tone curves TR1 and TR3 for the digestive organ (the stomach) and for the esophagus, which are indicated in FIG. 9 and FIG. 11, the parameters A1, A2, xd, and α are respectively set to −5, 500, 300, and 70. Furthermore, in FIG. 9, the parameters for the G tone curve TG1 are set to −28, 259, 100, and 45, and the parameters for the B tone curve TB1 are set to −17, 259, 110, and 40. Note that these values are used when the minimum value and the maximum value of the input values are 0 and 255.

The G tone curve TG1 is a curve with a form analogue to the letter "S", which intersects the line L at a point PG1 (x=x3). When denoting the G tone curve TG1 as y=fg1(x) (a function not restricted to the above-discussed function f(x)), the function fg1 satisfies the following conditions: fg1(x3)=x3 and fg1(x)<x for 0<x<x3, and fg1(x1)>x for x3<x<xm (=255). Furthermore, as for the derivative fg1'(x) of the fg1 (x), it satisfies the following conditions: fg1'(x1)=1 (0<x1<x3) and fg1'(x5)=1 (x3<x5<xm). Therefore, the output of the G signal is expanded when input signals are in a middle range XG1, (x1<x<x5 with x=x3 as the center of the expansion), and squashed in a low range, (0<x<x1) and also in a high range, (x5<x<xm). Note that x3 is set to a value smaller than the median of the histogram of the G component.

The B tone curve TB1 is also a curve with a form analogue to the letter "S", which intersects the line L at a point PB1 (x=x4>x3). When denoting the B tone curve TB1 as y=fb1(x) (this function not being restricted to the above-discussed function f(x)), the function fb1 satisfies the following conditions: fb1(x4)=x4 and fb1(x)<x for 0<x<x4, and fg1(x1)>x for x4<x<xm(=255). Furthermore, the derivative fb1'(x) of fb1(x) satisfies the following conditions: fg1'(x2)=1 (0<x2<x4) and fg1'(x6)=1 (x2<x6<xm). Therefore, the output of the B signal is expanded when input signals are in a middle range XB1 or x2<x<x6, with x=x4 as the center of expansion, and squashed in a low range, 0<x<x2, and in a high range, x6<x<xm. Note that x4 is set to a value smaller than the median of the histogram of the B component.

On the other hand, when denoting the function of the R tone curves TR1 and TR3 as y=fr1(x) (this function not being restricted to the above-discussed function f(x)), the function fr1 satisfies the following conditions: fr1(x)=x3 and fg1(x)<x for 0≦x≦xm. Furthermore, the derivative fr1'(x) of fr1(x) satisfies fr1'(x7)=1 (x6<x7<xm). Therefore, the output of the R signal is expanded when input signals are in a high range XR1(x7<x<xm), and squashed in a low range, x<x7. Note that in the present embodiment, the values of x1-x7 are ordered as in the order of their index notations.

Namely, in FIG. 9, at least the middle range XB1 for the B signal includes a range higher than the middle range XG1 for the G signal, or the middle range XG1 for the G signal includes a range lower than the middle range XB1 for the B signal, and the high range XR1 for the R signal includes a range higher than the middle ranges XG1 and XB1 for the is G and B signals. Furthermore, in the example of FIG. 9, the high range XR1 for the R signal does not overlap with the middle ranges XG1 and XB1 of the G and B signals.

Next, with reference to FIG. 10, features of the tone curves TR2, TG2, and TB2 for the large intestine will be explained. The tone curves TR2, TG2, and TB2 are represented by the above-discussed function f(x), with the parameters A1, A2, xd, and α respectively set to (0, 300, 200, 40), (−5, 350, 120, 30), and (−5, 350, 120, 30). Namely, in the example of FIG. 10, the G tone curve TG2 and the B tone curve TB2 are identical. However, in the present embodiment, the output value of tone curves TG2 and TB2 reaches the maximum value 255 at x=x11 and in x≧x11, y is a constant with a maximum value of 255.

The G and B tones TG2 and TB2 are curves with a form analogue to the letter "S", which intersect the line L at a point PG2(x=x9). When denoting the G and B tone curves TG2 and TB2 as y=f2(x) (this function not being restricted to the above-discussed function f(x)), the function f2 satisfies the following conditions: f2(x9)=x9 and f2(x)<x for 0<x<x9, and f2(x)>x for x9<x<xm(=255). Furthermore, the derivative f2'(x) of the f2(x) satisfies the following conditions; f2'(x8)=1 (0<x8<x9) and f2'(x)=0 for x11<x≦xm. Therefore, the output of the G and B signals are expanded when input signals are in a middle range XGB2, x8<x<x11 with x=x9 as the center of the expansion, and squashed in a low range, 0<x<x8, and also in a high range, x11<x<xm. Note that x9 is set to a value smaller than the medians of the histogram of the G and B components.

When denoting the function of the R tone curves TR2 as y=fr2(x) (this function not being restricted to the above-discussed function f(x)), the function fr2 satisfies the following condition: fr2(x)=x for 0≦x≦xm. Furthermore, in the case of the derivative fr2'(x) of fr2(x), it satisfies fr2'(x10)=1 (x9<x10<xm). Therefore, the output of the R signal is expanded when input signals are in a high range XR2 (x10<x<xm), and squashed in a low range, x<x10. Note that in the present embodiment, the values of x8-x11 are ordered in the order of their index notations.

Namely, in FIG. 10, at least the high range XR2 for the R signal included a range higher than the middle range XGB for the G and B signals. Furthermore, in the example of FIG. 10, the middle range XGB of the G and B signals overlaps with the high range XR2 of the R signal. Note that the tone curves TG3 and TB3 for the G and B components in the esophagus mode coincide with the line y=x.

As described above, according to the present embodiment, the Structural patterns or the blood vessel patterns in an image for observation are enhanced by transforming each of the R, G, and B color component histograms by controlling the tone curves of the R, G, and B signals, thereby enhancing features of a lesion area sufficiently even when using white light illumination in an electronic endoscope system.

Although in the present embodiment, the gradation compensation processes for the R, G, and B signals are carried out after the RGB conversion in the processing unit, the gradation compensation processes can be carried at any time after the analog front end processing and before an image is displayed. Furthermore, in the present embodiment, the selection of an observation mode or a target organ is carried out with the display device provided on the processing unit. However, the selection can also be carried out by a computer together with a monitor, which is connected to the processing unit.

Furthermore, according to the present embodiment, the user will not find it strange to compare a lesion-enhanced endoscopic image (an image subjected to the inventive gradation compensation processes) with a normal endoscopic image (an image not subjected to the inventive gradation compensation processes), since the luminance and the color tone throughout the image are virtually unaltered by the inventive gradation compensation of the prevent embodiment.

Although the embodiment of the present invention has been described herein with reference to the accompanying drawings, obviously many modifications and changes may be made by those skilled in this art without departing from the scope of the invention.

The present disclosure relates to subject matter contained in Japanese Patent Application No. 2008-177943 (filed on Jul. 8, 2008) and Japanese Patent Application No. 2008-274566 (filed on Oct. 24, 2008), which are expressly incorporated herein, by reference, in their entirety.

The invention claimed is:

1. An electronic endoscope signal-processing device, comprising:
a gradation compensation processor that compensates for R, G, and B gradations by controlling R, G, and B tone curves defining a relationship between input values and output values individually for R, G, and B signals; and
the R tone curve shaped so as to squash the output value of the R signal when the input value of the R signal is in a low range and to expand the output value of the R signal when the input value of the R signal is in a high range relative to the low range,
wherein the G tone curve is shaped so as to squash the output value of the G signal when the input value of the G signal is in a low range or in a high range, and to expand the output value of the G signal when the input value of the G signal is in a middle range, which is between the low and high ranges of the G signal,
wherein the B tone curve is shaped so as to squash the output value of the B signal when the input value of the B signal is in a low range or in a high range, and to expand the output value of the G signal when the input value of the B signal is in a middle range, which is between the low and high ranges of the B signal,
wherein at least the middle range of the B signal includes a range higher than the middle range of the G signal, or the middle range of the G signal includes a range lower than the middle range of the B signal, and
wherein the high range of the R signal does not overlap with the middle ranges of the G and B signals.

2. The electronic endo scope signal-processing device as claimed in claim 1, wherein the high range of the R signal includes a range higher than the middle ranges of the G and B signals.

3. An electronic endoscope system, comprising:
a gradation compensation processor that compensates for R, G, and B gradations by controlling R, G, and B tone curves defining a relationship between input values and output values individually for R, G, and B signals; and
the R tone curve is shaped so as to squash the output value of the R signal when the input value of the R signal is in a low range and to expand the output value of the R signal when the input value of the R signal is in a high range relative to the low range,
wherein the G tone curve is shaped so as to squash the output value of the G signal when the input value of the G signal is in a low range or in a high range, and to expand the output value of the G signal when the input value of the G signal is in a middle range, which is between the low and high ranges of the G signal,
wherein the B tone curve is shaped so as to squash the output value of the B signal when the input value of the B signal is in a low range or in a high range, and to expand the output value of the G signal when the input value of the B signal is in a middle range, which is between the low and high ranges of the B signal,
wherein at least the middle range of the B signal includes a range higher than the middle range of the G signal, or the middle range of the G signal includes a range lower than the middle range of the B signal, and
wherein the high range of the R signal does not overlap the middle ranges of the G and B signals.

4. The electronic endoscope signal-processing device, according to claim 1, wherein the electronic endoscope signal-processing device receives the R, G and B signals from an image obtained by photographing a stomach.

* * * * *